United States Patent [19]
Fine et al.

[11] Patent Number: 5,388,705
[45] Date of Patent: Feb. 14, 1995

[54] REJECTOR SYSTEM FOR CONVEYOR LINE

[75] Inventors: David H. Fine, Sudbury; Freeman W. Fraim, Lexington, both of Mass.

[73] Assignee: Thermedics Detection Inc., Woburn, Mass.

[21] Appl. No.: 23,327

[22] Filed: Feb. 26, 1993

[51] Int. Cl.6 ............................................. B07C 5/00
[52] U.S. Cl. .................... 209/524; 209/587; 209/651; 209/938; 198/367
[58] Field of Search ............... 209/523, 524, 585, 596, 209/651, 916, 938; 198/367, 367.1, 367.2, 368, 372, 389, 530; 356/23, 240, 428; 250/223 B, 224

[56] References Cited

U.S. PATENT DOCUMENTS

| | | | |
|---|---|---|---|
| 2,961,094 | 11/1960 | Bentley | 209/523 |
| 3,932,042 | 1/1976 | Faani et al. | 209/524 X |
| 4,158,624 | 6/1979 | Ford et al. | 209/523 |
| 4,280,624 | 7/1981 | Ford | 356/240 X |
| 4,550,820 | 11/1985 | Bishop | 198/389 |
| 4,750,620 | 6/1988 | Braschos | 209/651 X |
| 4,915,237 | 4/1990 | Chang et al. | 209/524 |

FOREIGN PATENT DOCUMENTS 3631879  3/1988  Germany ............... 209/523

Primary Examiner—D. Glenn Dayoan
Assistant Examiner—Tuan N. Nguyen
Attorney, Agent, or Firm—Fish & Richardson

[57] ABSTRACT

An in-line ram rejector system particularly for high speed bottling lines with unspaced plastic containers relies on a multi-beam optical system to keep track of the containers between a contamination detection station and a rejector station equipped with a ram rejector. The rejection station is also provided with an automatic side gate on the conveyor. When the leading edge of a tracked, identified container meets the beam, the side gate on the conveyor opens, and when the trailing edge of the same tracked identified container passes by the beam, the container, for example, a plastic beverage bottle is rammed out the open gate onto a neck rail, which catches the container upright.

55 Claims, 5 Drawing Sheets

REJECTOR SYSTEM FOR CONVEYOR LINE

BACKGROUND OF THE INVENTION

This invention relates to automatic systems for removing objects on an assembly line or conveyor.

In the past, conveyor lines of many different types have been equipped with various means for removing conveyed objects which have been identified as potentially defective. The systems that actually accomplish removal from the line, known generally as "rejectors" take several forms. The simplest, the ram rejector, involves a fast pneumatic cylinder alongside the conveyor that unceremoniously punches the offending object directly off the main conveyor line. The bottling industry has generally favored a more controlled approach.

One of the more widely used rejection systems in bottling lines involves a rotary take off system. Star wheels or vacuum wheels have selectively actuatable grippers which redirect selected individual bottles from the main conveyor line onto a separate reject conveyor like a rail spur while returning unaffected bottles to the main line. Rotary rejection systems, while offering more positive bottle control, are expensive, complicated, and often require spacing the bottles on the line. In addition, rotary systems take up a lot of space on the conveyor line. Consequently, they are not only expensive but difficult to retrofit into existing lines.

Greater attention has been focussed on rejection systems by one particular advance in bottling technology, namely the refillable, reusable plastic bottle. In many countries, particularly in Europe and South America, refillable plastic bottles are now in everyday use. Of course, refillable glass bottles have long been in use world-wide. Reusable plastic bottles are naturally far lighter and less fragile than glass. They have one shortcoming, however, that has slowed more widespread introduction. One of the plastics most often used for beverage bottles, namely polyethylene terephthalate or "PET", has a tendency, shared by most plastics, to absorb, over time, certain organic compounds, some more readily than others, contained in the substances with which the plastic comes in contact. In containers made of PET, these absorbed compounds can be gradually desorbed into the product to a degree which can potentially affect the quality of the product, depending on the type of product and storage conditions as well as the compound.

In extremely rare instances of misuse, reusable bottles come back to the bottler in dubious condition requiring special attention. Prior to refilling, of course, the returned bottles are thoroughly scoured and inspected. However, until now, on-line detection of residual contaminants before or after washing, which would be desirable because of desorption, has not been practical.

In a recent fortuitous development, competent, high speed, computerized chemical detection equipment is now becoming available at reasonable cost for sampling the air itself inside the bottles to distinguish the chemical composition of residues, on the fly, by analyzing vapors given off by the contaminants, without even slowing the bottles on the conveyor. But the advantage of on-line detection would be squandered if there were no cost-efficient means available for efficient in-line removal of the rare problem bottles after they are detected. With bottling lines running at speeds of 400 bottles per minute and up, even if detection is possible, cost effective, retrofittable bottle rejection systems compatible with these line speeds have not come to the fore to do the second half of the job. Given the sheer size of the installed investment in bottling lines all around the world, as well as the clear superiority of plastic bottles as beverage containers from the bottlers' standpoint, an efficient, low cost rejector system, compatible with the new detection technology, and easily retrofitted on existing bottling lines, would surely be much in demand.

SUMMARY OF THE INVENTION

The invention, in a general aspect, comprises an improved system for rejecting or removing individual objects, of which beverage bottles are but one example, from a continuously moving conveyor using a high speed rejector ram. In particular, with conveyed objects under so-called "line pressure", i.e., objects that are travelling tightly packed together on the line without any space between them, it has been discovered that a simple, fast-acting rejector ram can be arranged and operated to knock one object or even a series of objects in sequence out of the line and off the conveyor belt without affecting contiguous objects. With spaced or unspaced lines, the system preferably combines the ram rejector with a high speed automatic gate which opens just before the ram is fired. By judicious timing, the ram can be fired to strike the object in a manner that imparts stabilizing spin to help keep the object upright on its flight off the conveyor. In a preferred embodiment, the gate and ram are combined with a reject conveyor which is specially adapted to catch the rammed object in a way that it can be controllably conveyed away from the main line, preferably upright.

The system is particularly advantageous for use with on-line container inspection systems which look for defects in the container itself or its contents before or after filling or closure or capping. Specific examples of on-line inspection are systems which check for bottle fullness, cracks in the bottles, or improper capping, foreign objects, or contaminants. Machine vision systems open up many other possibilities. Many types of inspections result in practically instantaneous detection so that rejection can be accomplished by means of the rejector ram system according to the invention in real time. One inspection that does not presently permit instantaneous rejection is for chemical contaminants.

Thus, according to another aspect of the invention, in cases where rejection takes place downstream from detection, objects identified as having special properties are positively tracked from a detection station to a rejection station and rammed off the line, preferably onto a reject conveyor for further processing or disposal. At the rejection station, the identified objects are selectively rammed, for example by a high speed, pneumatic cylinder, off the conveyor in a manner such that adjacent qualified objects are freely conveyed past the rejection station.

In the preferred embodiment of the invention, the foregoing features are specifically implemented to deal with contaminated plastic bottles detected by a new air sampling analyzer for PET bottling lines. Many of these application specific features are nonetheless applicable to a broad range of containers and other conveyed objects. Thus the invention comprises the use of these features in bottling and other conveyor line applications, especially those having similar attributes.

In particular, the container or bottling rejection system, according to one aspect of the invention, relies on a multi-beam optical system to keep track of the bottles or other types of containers between the detection station and the ram rejector station. Several light beams are arranged in a series along the conveyor between the stations and aimed to intersect the conveyed objects, preferably a uniform portion of reduced width, namely, the neck of the bottle. One of the light beams is associated with the rejection station itself, and when an object identified by the detector crosses this beam, it triggers the ram rejector.

In the preferred system, the rejection station is also provided with an automatic side gate on the conveyor which is normally closed. In this system, when the leading edge of a tracked, identified object, for bottles preferably the neck, meets the beam, the side gate on the conveyor opens, and when the trailing edge of the same tracked identified object passes by the beam, the corresponding identified object gets rammed out the open side door.

The ram rejector in the preferred bottling system kicks the rejected bottle out the gate and onto the open end of a neck rail, which catches the bottle by an integral annular flange or collar formed on the bottle below the threaded top. This keeps the bottle upright.

In addition, by striking the bottle approximately at the center of gravity, vertically, but a little off center, the ram can impart spin to stabilize the bottle in flight to the neck rail. Spin also helps speed the bottle down the neck rail.

In another aspect of the invention, the rejection system is provided with means for dealing more harshly with severely contaminated bottles or other types of containers by diverting them to a destructive disposal unit which renders them permanently nonreusable. In this system, the detection station discriminates between contaminated and badly contaminated bottles and identifies the bottles accordingly. The badly contaminated bottles are either diverted from the neck rail by appropriate rail switching apparatus or by a second ram rejector station on the conveyor, downstream from the first. To ensure that all contaminated bottles are rejected, the optical tracking system is extended to the neck rail switch or second rejection station, which operates otherwise similarly to the first rejection station. The second ram rejector station can also be used to provide redundancy in case the first station is temporarily disabled.

The invention offers the advantage of simple, reliable, low cost, but certain removal of the rare bottle requiring special processing without having to stop the line or space the bottles. The in-line tracking ram rejector system offers reliable rejection of bad bottles while operating at existing line conditions with line pressure, i.e., spaced or unspaced bottles. The design is particularly compatible with current high speed bottle washing and filling conveyors and requires a minimum of modification to an existing line to install. In cooperation with the automatic gate, the ram knocks a clean hole in the line without affecting the other bottles. By keeping the bottles upright and intact during the high speed transfer, spillage and splash are minimized. Moreover, providing for automatic termination of badly contaminated bottles goes a long way toward eliminating the small but ever present risk of operators deliberately defeating the aim of the system. Many of the same or similar advantages are achievable in other applications besides contaminant detection on bottling or other conveyor lines.

DESCRIPTION OF THE PREFERRED EMBODIMENTS

Figure 1:
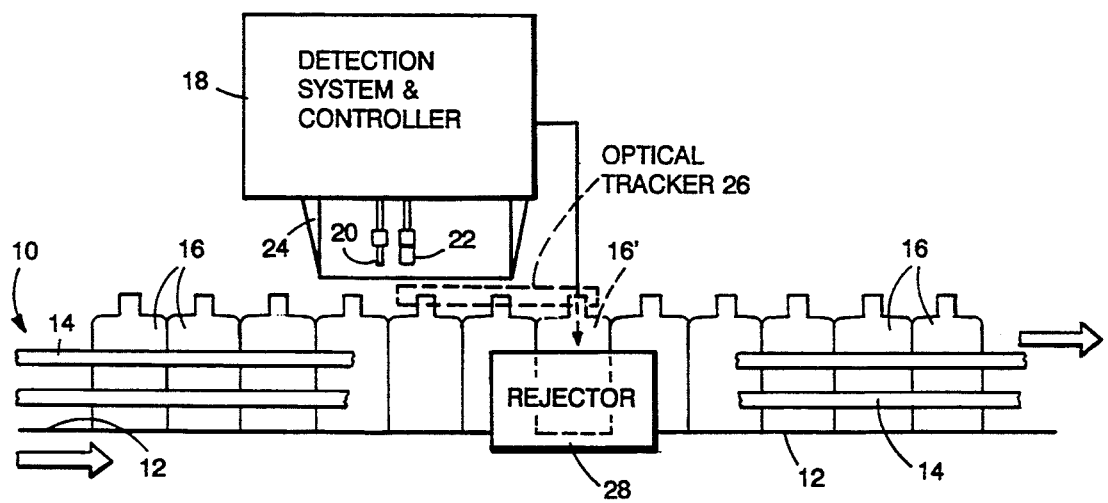
FIG. 1 is an overall block diagram of the in-line tracking ram rejector system, according to a preferred application of the invention, in a bottling line with an on-line automatic contaminant detection system.
Figure 2:
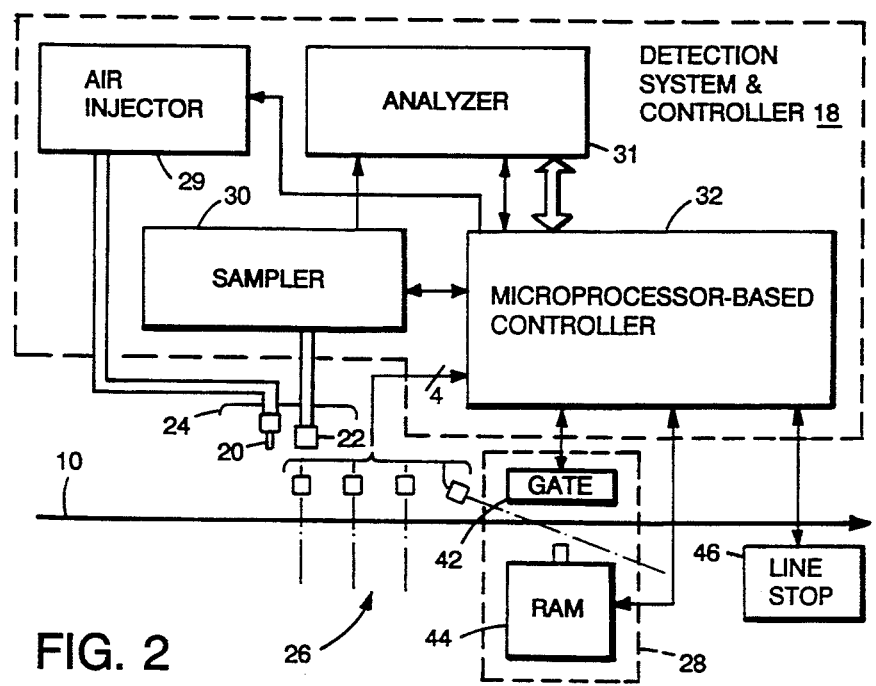
FIG. 2 is a more detailed block diagram of the detection system, controller, tracking and rejector subsystems of FIG. 1.
Figure 3:
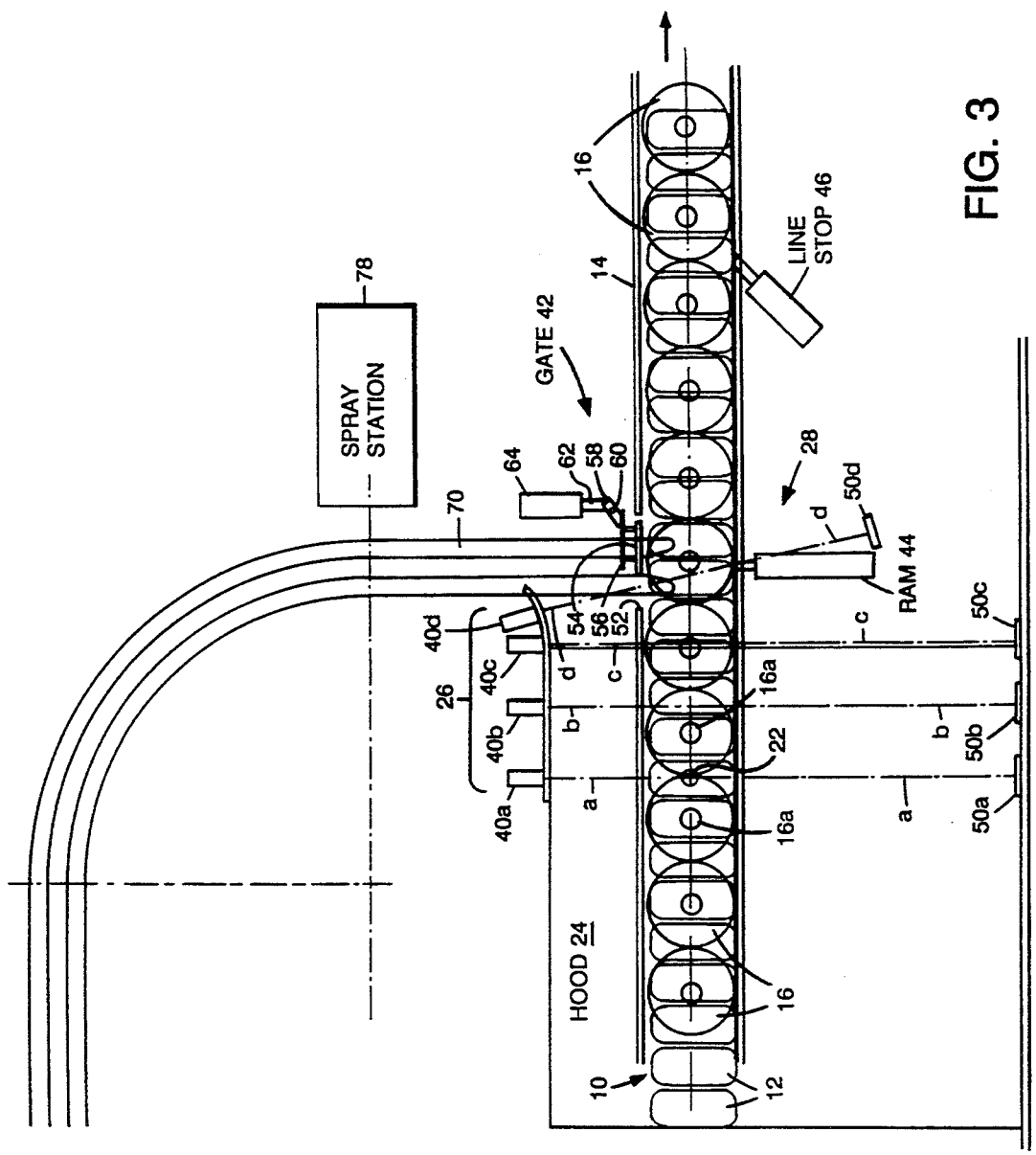
FIG. 3 is a plan diagrammatic view showing the layout of the components of the tracking and rejection subsystems of FIG. 1.

FIGS. 1 and 3 show a conventional bottling line conveyor 10 with link belt 12 and guard rails 14. On the conveyor 10 is a series of contiguous, open-top, plastic (e.g, PET) beverage bottles 16. The bottles 16 are all returns. The so-called "line" comprising the moving series of bottles 16 on the conveyor 10 travels at speeds of from zero to 1000 bottles per minute, preferably about 400 bottles per minute at a substantially constant rate. The portion of the line shown in FIGS. 1 and 2 may come before or after the washing station, or between washing stations or cycles prior to refilling.

With the bottles pressed together in the manner shown in FIGS. 1 and 3, the entire line of bottles experiences line pressure on the order of from a few pounds up to as much as forty pounds. That is, each bottle may be tightly squeezed between the two adjacent bottles. Line pressure is desirable in general as it helps keep the bottles from tipping over and maximizes throughput, while keeping the line running smoothly. However, gaps do occur and the detection and rejection systems described herein are designed to accommodate spaced as well as unspaced bottles, in any pattern.

As shown in FIG. 1, the bottles 16 first pass through a detection system and controller 18 which examines the contents of each passing bottle for possible contamination. A suitable detection system product for beverage bottling lines is available from Thermedics Detection, Inc. of Woburn, Massachusetts under the trademark Alexus ™. Other compatible types of contaminant detection systems can be used. The detection system 18, as shown in FIG. 1, is equipped with an air injection nozzle 20 and a sample inlet 22 mounted in juxtaposition under a hood 24 directly above the line of bottles. The air injection nozzle 20 is aimed to inject puffs of air into the open tops of bottles 16 as they file by below.

The bottles 16 are tracked by an optical tracking system 26 which extends from the sample inlet 22 to a rejector station 28 where a contaminated bottle 16' discovered by the detection system 18 is knocked out of the line.

The major components of the detection system 18 are shown in FIG. 2. An air injector 29 produces pulses of air pressure to puff heated or unheated air or some other inert gas into the open top of a bottle as it passes beneath the injector nozzle 20. A sample cloud is released above the bottle, and an air sample from the cloud is withdrawn through sample inlet 22 by an evacuator sampler 30. A portion of the withdrawn sample is passed from the sampler to a residue analyzer 31, the remainder of the evacuated sample being vented or passed back to the air injector. The analyzer 31 conducts an analysis of the sample on the spot for the presence of contaminants, indicated for example by nitrogen compounds in the sample cloud, by means of a chemiluminescence technique. The analyzer 31 issues a signal indicating the magnitude of any detected contaminant to a microprocessor-based controller 32.

Controller 32 is a programmable computer configured and equipped with input and output features to operate the detector and rejection systems. Controller 32 issues commands to the various components based on programmed timing and inputs from optical tracker system 26 as well as from the analyzer 31.

The rejector station 28 includes a side gate 42 forming a controllable opening in the conveyor line and a pneumatic piston ram rejector 44, both of which are controlled by respective output commands from the controller 32. An emergency line stop 46, also operated by the controller 32, is available in case of detector or rejector station failure. In addition, the line stop is activated when a filter on the detection system needs changing.

The component layout of the optical tracker 26, gate 42, ram rejector 44 and line stop 46 is shown in more detail in FIG. 3. In this particular implementation, optical tracker 26 uses four light beams a, b, c and d indicated by dot-dash lines in FIG. 3. The beams are generated by light emitter and detector units 40a, 40b, 40c, and 40d. Each emitter/detector unit is aimed across the conveyor to bounce a beam of light off corresponding reflectors 50a, 50b, 50c and 50d, as shown in FIG. 3. The emitter/detector units are conveniently mounted to the hood 24 so that the beam axes are all approximately coplanar and are at an elevation above the conveyor belt 12 to intercept the middle portion of the threaded necks 16a of the bottles.

The first light beam a is aligned with the sample inlet 22 of the detection system. At the instant depicted in FIGS. 1 and 3, the sample inlet 22 happens to be positioned at the tangency between two bottles. Two and one-half bottle diameters downstream from the sample inlet 22 on the conveyor 10 is the rejector station 28. The distance between the sample and rejector stations can be a minimum, however, of one and one-half bottle diameters. However, two and a half diameters is preferred for two reasons. First the detection decision takes at least 200 ms from the time the bottle is dead center under the sampler 22. During this time a 1.5 liter bottle with a diameter of 3.5 inches moves nearly one and a half diameters. Exceeding this spacing introduces a safety factor allowing for a delay in the detection decision. Second, moving the rejector station farther away from the detection area reduces the risk that splash from the rammed bottle will contaminate the hood. Two and a half diameters spaces the rejection station far enough away to avoid this.

The rejection station comprises two major components, the gate 42 in the rail 14 and the ram rejector 44 which are positioned on opposite sides of the conveyor 10. The purpose of the gate 42 is to keep the rail in place so as to maintain line pressure. In most applications the line runs with contiguous bottles under enough pressure that a large enough gap in the rail for a bottle pass through would allow one of the bottles to pop out of the line on its own. This is strictly prohibited by opening the gate only when and for as long as necessary to reject a bottle.

Gate 42 is implemented by cutting away a gap in the guard rail 14 to form an opening 52 in the side of the conveyor and then mounting a excised portion of the rail forming the door to a bell crank assembly consisting of a bracket 56 to which the rail door 54 is mounted in parallel and an angled arm 58 pivoted at point 60. The end of arm 58 is also pivotally connected to a piston 62, which extends from linear actuator 64 operated by the controller 32 (FIG. 2). The pivoted assembly has low mass (i.e., low angular inertia) to allow fast actuation (i.e., angular acceleration). Fully open, the gate of the preferred embodiment only achieves an angle of 70 degrees with the conveyor, however, this is sufficient for the bottle to clear as the gate is offset slightly downstream of the ram axis. The gaps on either side of the closed gate 42, as shown in FIG. 3, are much smaller than the bottle diameter and therefore afford no opening for the bottles.

Across from the gate 42, the ram rejector or ram 44 is mounted perpendicularly to the conveyor and at an elevation above the belt to strike the bottle approximately at its center of gravity. Ram 44 is preferably a pneumatic cylinder with a four inch stroke. As the conveyor belt width is only about three and a half inches, the piston thus is capable of extending all the way across the conveyor belt.

A neck rail 70 is disposed in alignment with the ram 44 beginning above the gate 42 as shown in FIG. 3. Neck rail 70, is positioned such that the open end of the neck rail catches the rejected bottle as the bottle is rammed off the conveyor by the ram 44. The neck rail may slope downward so as to take advantage of gravity feed. The purpose of the neck rail 70 is to convey the rejected bottles away from the conveyor line to another location where the bottles may be subjected either to more rigorous cleaning or discarded. Suitable neck rail conveyor systems are commercially available from Aidlin Automation, Inc. of Florida.

Figure 4:
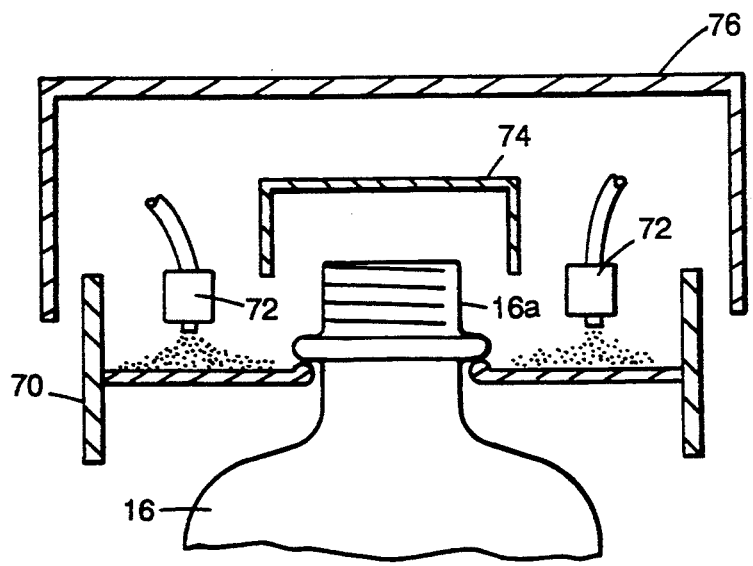
FIG. 4 is a detail diagrammatic view, in elevation, of the neck rail catching a bottle by the neck.

As shown in FIG. 4, the neck rail 70 is comprised of two opposed T-beams each having an outer vertical frame member and an inner flat horizontal rail with edge beading on which the annular flange of the bottle neck 16a can ride. The rail is preferably equipped with injectors 72 for soapy water to clean and lubricate the rails. Inner and outer shields 74 and 76 are disposed as shown in FIG. 4 to help retain volatile emissions and splashes from bottles which contain liquid agitated or released by the abrupt action of the ram. A spray station 78 with a vertical spray bar (not shown) is located along the neck rail 70.

With reference again to FIG. 3, the array of light beams a, b, c and d is established so that there are enough sensors (the beams act as sensors) between the sampling point and the rejection point that the distance between the sensors, i.e., between the points at which the beams intersect the centerline of the conveyor 10, is less than a bottle width. This requirement assures that each sensor beam is tracking only one bottle at a time. This allows the software to follow a bottle from the sampling point 22 to the rejection point 28 regardless of line speed. The preferred distance between the beams has been established at about two thirds of the full width of a bottle.

A sensor beam will be uninterrupted and thus "on" when there is no bottle in the path of the beam. The term "front side" or "leading edge" will refer to the condition when the bottle initially encounters and breaks a beam. The term "back side" or "trailing edge" will refer to the condition when the bottle leaves a sensor and the beam is re-established.

Figures 5A, 5B, 5C, 5D, 5E:
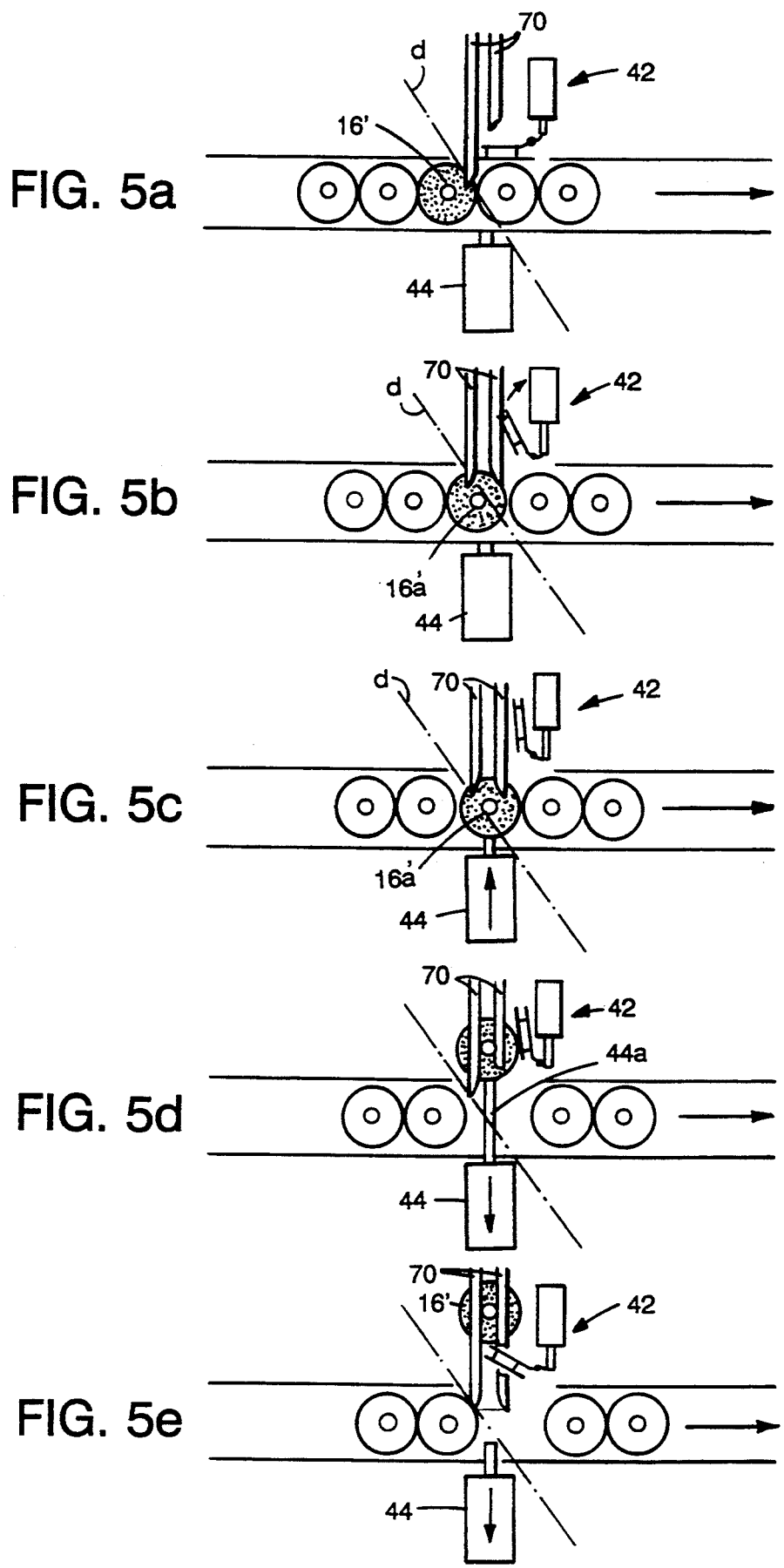
FIG. 5 is a series of five sequential, simplified plan diagrammatic views of the rejector station of FIG. 1–3 in action.

The most upstream sensor beam a is the bottle sensor. This is the sensor which will first see a bottle when it enters the system. This is also the location 22 at which a sample is taken. The bottle sensor is followed by a number of tracking sensor beams in the present example two, namely b and c, which serve to follow the bottle from the sampling point (bottle sensor) to the reject sensor (beam d). The location of the reject sensor beam d is very important as it controls the opening of the gate 42 and the firing of the ram rejector 44. When a contaminated bottle is at the front side of the reject sensor, as represented by the stippled bottle 16' shown in FIG. 5b whose neck is just touching the reject sensor beam d, the gate 42 will be thrown open. The ram rejector 44 is fired, with the gate already open when bottle 16' which has been marked for rejection as discussed below, is at the back side of the sensor, i.e., the trailing edge of the bottle neck 16a clears the beam d, as shown in FIG. 5c. The gate remains open for a programmable gate period long enough for the rejected bottle to escape on the neck rail and clear the gate 42, as shown in FIGS. 5d and 5e.

In the software running on the microprocessor controller, a bottle record is used to describe the status of each bottle that is present and accounted for in the optical tracking system 26. This record contains a yes/no status which indicates if the bottle should be rejected. When a bottle enters the tracking system at the front side of the bottle sensor (beam a, FIG. 3), a new bottle record is created. An identifier for this record is passed on to the analysis software to indicate that this is the bottle which is currently being analyzed. If the analysis software decides that this bottle should be rejected, it will use the record identifier to find the proper bottle record and then mark this bottle for rejection. A bottle record is passed from upstream to downstream sensor at the backside of the upstream sensor. When a sensor receives a bottle record, so to speak, it will be waiting for that bottle, and once it sees the bottle, it will pass the record on to the next sensor. The bottle record will propagate through the tracking system as the bottle passes through each successive sensor. The bottle record eventually reaches the reject sensor (beam d) at which time the bottle will be rejected if the bottle record has been marked for rejection by the application software.

Error detection software assures that the sensors are properly aligned. Incorrect alignment of a sensor would cause the sensor to fail to see a bottle or to see the bottle too early. These conditions are checked for when a bottle record is passed from sensor to sensor. Because the distance between sensors must be less than one full bottle width, a sensor can only be waiting for one bottle at a time. If a sensor is already waiting for a bottle when its upstream sensor is trying to pass it a bottle, then an error has resulted.

In the case of bottle wobble, any sensor that sees a bottle which it is not waiting for, will ignore that bottle. This would happen if a bottle, which had just passed through a sensor, rocked back and re-activated that sensor.

The opening and closing interval of the gate 42 and the full return stroke interval of the ram are critical. As the bottles are moving at a rate of about 400 per second, given a bottle full outer diameter of 3.6 inches, the one inch neck traverses the reject sensor beam in about 50 milliseconds (ms). The gate triggered by the leading edge of the neck should open within the 50 ms to be ready for the bottle ejection. The full stroke of the piston of the ram 44 is about 4 inches. The piston must make it across the conveyor and back before the next bottle in the line arrives. The half diameter bottle distance is traversed by the next bottle in about 75 ms, thus if the ram is designed to go out and back in, say, less than 50 to 60 ms, this should be ample time to clear the next bottle. Commercial four inch rams with round-trip stroke intervals of 30 ms are available.

The timing of the firing of the ram rejector can be controlled in two ways, either by adjusting the beam d or by programming a delay into the firing command. In this manner the firing can be adjusted so that the bottle is struck slightly off center in a manner that imparts spin about the bottle axis. This has two potential benefits. First, the spinning action stabilizes the bottle like a toy gyroscope and helps keep it upright as it travels to the neck rail. Maintaining the bottle upright in a spinning condition tends to further minimize spillage. Second the spinning tends to make the bottle settle onto and slide down the rail faster.

Figure 6:
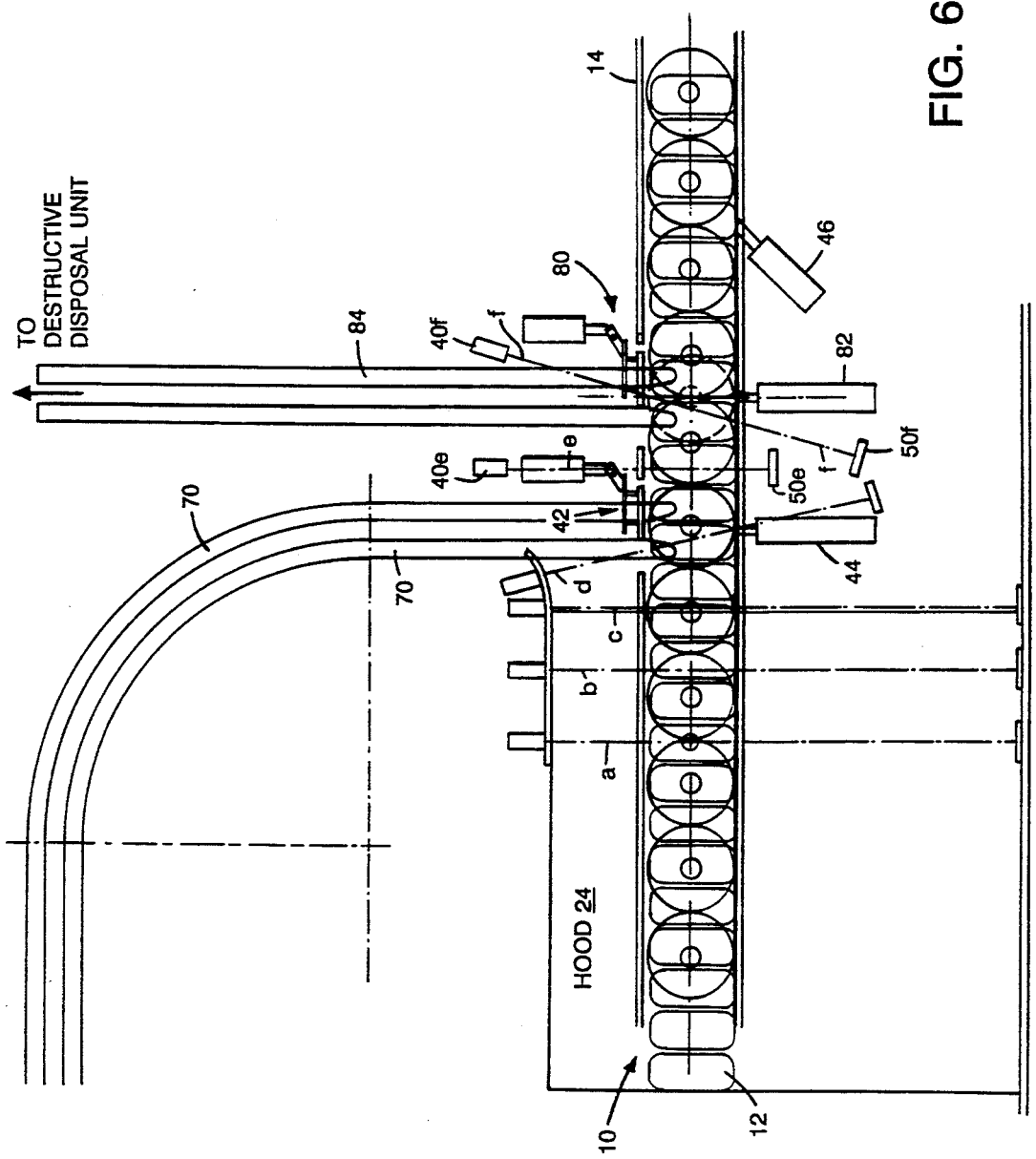
FIG. 6 is a plan diagrammatic view of an alternative embodiment with a dual in-line tracking ram rejector system.

FIG. 6. illustrates a fancier implementation having a pair of rejector stations. A second rejector station outfitted with gate 80 and ram rejector 82 is located one and a half bottle widths from the first rejector station. In order to extend the tracking system to the second rejector station, emitter/detector units 40e and 40f along with opposed reflectors 50e and 50f are added, as shown, to establish sensor beams e and f. Beam e is another intermediate tracking sensor while beam f acts as a second reject sensor. These two additional beams e and f function in a manner similar to beams c and d. In addition, the second rejector station is equipped with a second neck rail 84, which is routed to transport the rejected bottle to a destructive disposal unit where badly contaminated bottles are punctured, crushed or have their necks split by driving a wedge into the open top of each bottle.

The dual rejector system serves to discriminate effectively between treatment of contaminated bottles and badly contaminated bottles. If the analyzer software decides that a reading is too high, i.e., above some peak threshold, then the bottle record is marked differently so that rejection occurs at the second rejector station rather than the first.

Figure 7:
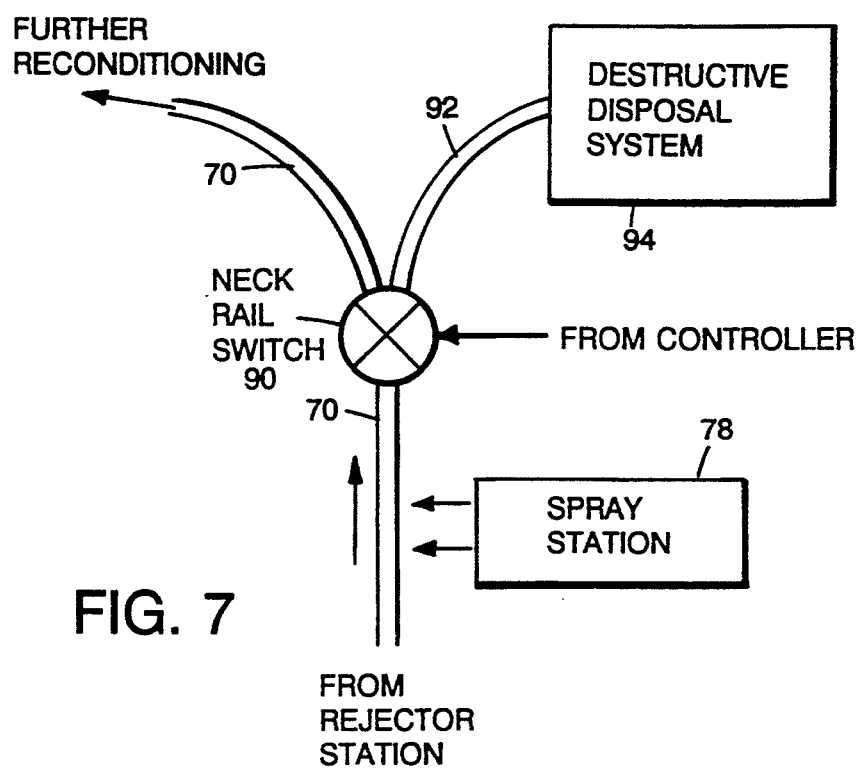
FIG. 7 (on the sheet with FIG. 4) is a schematic diagram of the layout of a neck rail diverter system as an alternative dual rejection system.

FIG. 7 shows an alternate method of providing different treatment for severely contaminated bottles. The bottle record is equipped with a further indication that the bottle after rejection should be shunted via neck rail switch 90 to a neck rail spur 92 which leads to a destructive disposal system 94 of the type described above. Suitable automatic neck rail switching equipment is available from Aidlin Automation, Inc.

Other embodiments are within the following claims. In particular, while the foregoing description has been geared to beverage bottling lines, the system is adaptable, in whole or in part, to other conveyor rejector applications without departing from the spirit of the invention.

What is claimed is:

1. A method of rejecting individual objects on a continuously moving conveyor having a detection station and a rejection station, comprising:

continuously conveying a series of substantially uniform objects on the conveyor past the detection station;

at the detection station identifying a passing object on the conveyor as having a special property;

continuously conveying the identified object on the conveyor along with the series of objects to the rejection station in the same manner and condition as adjacent objects on the conveyor while positively tracking the identified object between the detection station and the rejection station by optically tracking the identified object from the detection station to the rejection station with a series of light beams arranged along the conveyor between the stations without stopping or forcibly spacing the conveyed objects at any point between the stations; and at the rejection station selectively ramming the identified object off the conveyor such that adjacent objects are freely conveyed past the rejection station.

2. The method of claim 1, further comprising catching the rammed object on a reject conveyor to transport the rammed object to another location apart from the original conveyor.

3. The method of claim 2, further comprising the step of maintaining the rammed object upright while catching the rammed object on the other conveyor.

4. The method of claim 1, further comprising associating one of the light beams with the rejection station itself, and responsive to intersection of the beam with a tracked identified object, triggering the ramming of the corresponding identified object.

5. The method of claim 1, further comprising associating one of the light beams with the rejection station itself, and responsive to intersection of the beam with a leading edge of a tracked identified object, opening a side gate on the conveyor, and responsive to intersection of the beam with a trailing edge of the tracked identified object, triggering the ramming of the corresponding identified object out the open side door.

6. The method of claim 1, wherein each of said objects has a uniform portion of reduced width, said method further comprising aiming the series of light beams across the conveyor to intersect said uniform portion of reduced width on each passing object.

7. The method of claim 6, further comprising spacing the light beams apart by less than the full width of said objects in the direction of the conveyor.

8. The method of claim 1, further comprising opening a side gate on the conveyor at the rejection station just before ramming the identified object so that the identified object is rammed out the side gate, and immediately closing the side gate after the rammed object has cleared the gate.

9. A method of rejecting individual objects on a continuously moving conveyor having a detection station and a rejection station and selectively diverting the objects, comprising:

continuously conveying a series of substantially uniform objects on the conveyor past the detection station;

at the detection station identifying a passing object on the conveyor as having a first or second special property;

continuously conveying the identified object on the conveyor along with the series of objects to the rejection station in the same manner and condition as adjacent objects on the conveyor while positively tracking the identified object between the detection station and the rejection station without stopping or forcibly spacing the conveyed objects at any point between the stations;

at the rejection station selectively ramming the identified object off the conveyor such that adjacent objects are freely conveyed past the rejection station, catching the rammed object on a first reject conveyor to transport the rammed object to another location apart from the conveyor; and diverting the rammed object off of the first reject conveyor if the rammed object was identified at the detection station as having said second property by switching the rammed diverted object to a second reject conveyor for removal to a location apart from the original conveyor and first reject conveyor.

10. A method of rejecting individual objects on a continuously moving conveyor having a detection station and first and second rejection stations, comprising:

continuously conveying a series of substantially uniform objects on the conveyor past the detection station;

at the detection station identifying a passing object on the conveyor as having a first or second special property;

continuously conveying the identified object on the conveyor along with the series of objects to the first rejection station in the same manner and condition as adjacent objects on the conveyor while positively tracking the identified object between the detection station and the first rejection station without stopping or forcibly spacing the conveyed objects at any point between the stations;

at the first rejection station selectively ramming an object identified as having the first property off the conveyor such that adjacent objects which have not been so identified are freely conveyed past the first rejection station, and;

continuously conveying an object identified as having the second property on the conveyor along with the series of objects to the second rejection station in the same manner and condition as adjacent objects on the conveyor while positively tracking the identified object between the first and second rejection stations without stopping or forcibly spacing the conveyed objects at any point between the stations;

at the second rejection station selectively ramming an object identified as having the second property off the conveyor such that adjacent objects which have not been so identified are freely conveyed past the second rejection station.

11. The method of claim 10, further comprising catching an object rammed at the first rejection station on a first reject conveyor to transport the rammed object to another location apart from the original conveyor, and catching an object rammed at the second rejection station on a second reject conveyor to transport the rammed object to another location apart from the first conveyor.

12. A system for rejecting individual objects on a continuously moving conveyor having a detection station and a rejection station, comprising:
- a conveyor for conveying a series of substantially uniform objects in a line along a conveyor path at a substantially constant speed;
- a detection station located on the conveyor path for identifying a passing object on the conveyor as having a special property;
- a rejection station located on the conveyor path at a predetermined spacing from the detection station;
- said conveyor continuously conveying the identified object on the conveyor along with the series of objects to the rejection station in the same manner and condition as adjacent objects on the conveyor without stopping or forcibly spacing the conveyed objects at any point between the stations;
- an optical tracker including a series of light beams arranged along the conveyor between the detection station and the rejection station to positively keep track of the identified object from the detection station to the rejection station and for initiating a trigger command; and
- said rejection station having a ram responsive to said trigger command for selectively ramming an identified object off the conveyor such that adjacent objects are freely conveyed past the rejection station.

13. The system of claim 12, further comprising a reject conveyor for catching the rammed object to transport the rammed object to another location apart from the original conveyor.

14. The system of claim 13, wherein said reject conveyor maintains the rammed object upright while catching and transporting the rammed object.

15. The system of claim 12, wherein one of the light beams is associated with the rejection station itself, and said tracker is operable to initiate said trigger command in response to intersection of the beam with a tracked identified object, triggering the ramming of the corresponding identified object.

16. The system of claim 12, wherein each of said objects has a uniform portion of reduced width, and wherein said light beams are aimed across the conveyor to intersect said uniform portion of reduced width on each passing object.

17. The system of claim 16, wherein said light beams are spaced apart by less than the full width of said objects in the direction of the conveyor.

18. The system of claim 12, further comprising a side gate on the conveyor at the rejection station, and means for opening the gate just before ramming the identified object so that the identified object is rammed out the side gate, and immediately closing the side gate after the rammed object has cleared the gate.

19. The system of claim 12, wherein one of the light beams is associated with the rejection station itself, and said tracker initiates a gate command responsive to intersection of the beam with a leading edge of a tracked identified object, said opening means responsive to said gate command for opening said side gate on the conveyor, and said tracker responsive to intersection of the beam with a trailing edge of the tracked identified object issuing said trigger command, triggering the ramming of the corresponding identified object out the open side door.

20. A system for rejecting individual objects on a continuously moving conveyor having a detection station and a rejection station and selectively diverting the objects, comprising:
- a conveyor for conveying a series of substantially uniform objects in a line along a conveyor path at a substantially constant speed;
- a detection station located on the conveyor path for identifying a passing object on the conveyor as having a first or second special property;
- a rejection station located on the conveyor path at a predetermined spacing downstream from the detection station;
- said conveyor continuously conveying the identified object on the conveyor along with the series of objects to the rejection station in the same manner and condition as adjacent objects on the conveyor without stopping or forcibly spacing the conveyed objects at any point between the stations;
- an optical tracker to positively keep track of the identified object between the detection station and the rejection station and for initiating a trigger command; and
- said rejection station having a ram responsive to said trigger command for selectively ramming an identified object off the conveyor such that adjacent objects are freely conveyed past the rejection station;
- first and second reject conveyors; means for catching the rammed object on the first reject conveyor to transport the rammed object to another location apart from the conveyor; and
- means for diverting the rammed object off of the first reject conveyor if the rammed object was identified at the detection station as having said second property by switching the rammed diverted object to the second reject conveyor for removal to a location apart from the original conveyor and first reject conveyor.

21. A system of rejecting individual objects on a continuously moving conveyor having a detection station and first and second rejection stations, comprising:
- a conveyor for conveying a series of substantially uniform objects in a line along a conveyor path at a substantially constant speed;
- a detection station located on the conveyor path for identifying a passing object on the conveyor as having a first or second special property;
- first and second rejection stations located on the conveyor path at predetermined spacings downstream from the detection station;
- said conveyor continuously conveying the identified object on the conveyor along with the series of objects to the first and second rejection stations in the same manner and condition as adjacent objects on the conveyor without stopping or forcibly spacing the conveyed objects at any point between the stations;
- an optical tracker to positively keep track of the identified object between the detection station and the first and second rejection stations and for initiating a trigger command;
- said first rejection station having a ram responsive to said trigger command for selectively ramming an object identified as having the first property off the conveyor such that adjacent objects are freely conveyed past the rejection station; and said second rejection station having a ram responsive to said trigger command for selectively ramming an object identified as having the second property off the conveyor such that adjacent objects are freely conveyed past the rejection station.

22. The system of claim 21, further comprising first and second reject conveyors arranged respectively to catch an object rammed at the first rejection station to transport the rammed object to another location, and to catch an object rammed at the second rejection station to transport the rammed object to another location.

23. Apparatus for rejecting unspaced objects on a continuous high speed conveyor with line pressure, comprising:

a detector situated on the conveyor line to examine each passing object in order to identify an object to be rejected;

a rejection station on the conveyor having a rejector ram mounted to one side of the conveyor with a piston directed across the conveyor line to ram the identified object out of the line and off of the conveyor;

a side gate on the conveyor at the rejection station opposite the rejector ram; and means for opening the gate just before ramming the identified object with the rejector ram so that the identified object is rammed out the side gate, and for closing the side gate after the rammed object has cleared the gate;

said rejector ram and said gate being operable to reject the identified object from the conveyor without stopping or substantially affecting travel of contiguous objects which were in contact under line pressure with the identified object, prior to its rejection, such that the contiguous objects are freely conveyed past the rejection station.

24. The apparatus of claim 23, further comprising a reject conveyor approximately parallel to the piston of the rejector ram for catching the rammed object to transport the rammed object to another location apart from the original conveyor.

25. The apparatus of claim 24, wherein said reject conveyor maintains the rammed object upright while catching and transporting the rammed object.

26. The apparatus of claim 25, wherein said objects are plastic bottles and said reject conveyor is a neck rail.

27. Apparatus for rejecting objects on a conveyor, comprising:

a detector situated on the conveyor line to examine each passing object in order to identify an object to be rejected; and a rejection station on the conveyor having an automatic side gate arranged on one side of the conveyor, a rejector ram mounted opposite the gate on the other side of the conveyor with a piston directed across the conveyor line to ram the identified object out of the line through the gate and off of the conveyor, and means for opening the gate just before ramming the identified object with the rejector ram and for closing the gate after the rammed object has cleared the gate, said rejector ram and said gate being operable to reject the identified object from the conveyor without stopping or substantially affecting travel of contiguous objects which were in contact under line pressure with the identified object.

28. The apparatus of claim 27, further comprising a reject conveyor approximately parallel to the piston of the rejector ram for catching the rammed object to transport the rammed object to another location apart from the original conveyor.

29. The apparatus of claim 28, wherein said reject conveyor maintains the rammed object upright while catching and transporting the rammed object.

30. The apparatus of claim 29, wherein said objects are plastic bottles and said reject conveyor is a neck rail.

31. A method of rejecting contaminated containers on a continuously moving high speed conveyor having a detection station and a rejection station, comprising:

continuously conveying a series of substantially uniform uncapped containers on the conveyor past the detection station;

at the detection station identifying a passing container on the conveyor as contaminated;

continuously conveying the identified container on the conveyor along with the series of containers to the rejection station in the same manner and condition as adjacent containers on the conveyor while positively tracking the identified container between the detection station and the rejection station by optically tracking the identified container from the detection station to the rejection station with a series of light beams arranged along the conveyor between the stations without stopping or forcibly spacing the conveyed containers at any point between the stations; and at the rejection station selectively ramming the identified container off the conveyor such that adjacent containers are freely conveyed past the rejection station.

32. The method of claims 31, further comprising catching the rammed container on a reject conveyor to transport the rammed container to another location apart from the original conveyor.

33. The method of claim 32, further comprising the step of maintaining the rammed container upright while catching the rammed container on the reject conveyor.

34. The method of claim 31, further comprising associating one of the light beams with the rejection station itself, and responsive to intersection of the beam with a tracked identified container, triggering the ramming of the corresponding identified container.

35. The method of claim 31, further comprising associating one of the light beams with the rejection station itself, and responsive to intersection of the beam with a leading edge of a tracked identified container, opening a side gate on the conveyor, and responsive to intersection of the beam with a trailing edge of the tracked identified container, triggering the ramming of the corresponding identified container out the open side door.

36. The method of claim 31, wherein each of said containers has a uniform portion of reduced width, said method further comprising aiming the series of light beams across the conveyor to intersect said uniform portion of reduced width on each passing container.

37. The method of claim 31, further comprising spacing the light beams apart by less than the full width of said containers in the direction of the conveyor.

38. The method of claim 31, further comprising opening a side gate on the conveyor at the rejection station just before ramming the identified container so that the identified container is rammed out the side gate, and immediately closing the side gate after the rammed container has cleared the gate.

39. A method of rejecting individual containers on a continuously moving high speed conveyor having a detection station and a rejection station and selectively diverting the containers, comprising:

continuously conveying a series of substantially uniform containers on the conveyor past the detection station;

at the detection station identifying a passing container on the conveyor as having a first or second level of contamination;

continuously conveying the identified container on the conveyor along with the series of containers to the rejection station in the same manner and condition as adjacent containers on the conveyor while positively tracking the identified container between the detection station and the rejection station without stopping or forcibly spacing the conveyed containers at any point between the stations;

at the rejection station selectively ramming the identified container off the conveyor such that adjacent containers are freely conveyed past the rejection station, catching the rammed container on a first reject conveyor to transport the rammed container to another location apart from the conveyor; and diverting the rammed container off of the first reject conveyor if the rammed container was identified at the detection station as having said second level of contamination and rendering the container nonreusable.

40. The method of claim 39, wherein the step of diverting is accomplished by switching the rammed diverted container to a second reject conveyor for removal to a location apart from the original conveyor and first reject conveyor.

41. A method of rejecting individual containers on a continuously moving high speed conveyor having a detection station and first and second rejection stations, comprising:

continuously conveying a series of substantially uniform containers on the conveyor past the detection station;

at the detection station identifying a passing container on the conveyor as having a first or second special property;

continuously conveying the identified container on the conveyor along with the series of containers to the first rejection station in the same manner and condition as adjacent containers on the conveyor while positively tracking the identified container between the detection station and the first rejection station without stopping or forcibly spacing the conveyed containers at any point between the stations;

at the first rejection station selectively ramming an container identified as having the first property off the conveyor such that adjacent containers which have not been so identified are freely conveyed past the first rejection station, and;

continuously conveying a container identified as having the second property on the conveyor along with the series of containers to the second rejection station in the same manner and condition as adjacent containers on the conveyor while positively tracking the identified container between the first and second rejection stations without stopping or forcibly spacing the conveyed containers at any point between the stations;

at the second rejection station selectively ramming a container identified as having the second level of contamination off the conveyor such that adjacent containers which have not been so identified are freely conveyed past the second rejection station; and rendering the rammed container identified as having the second level of contamination nonreusable.

42. The method of claim 41, further comprising catching a container rammed at the first rejection station on a first reject conveyor to transport the rammed container to another location apart from the original conveyor, and catching a container rammed at the second rejection station on a second reject conveyor to transport the rammed container to another location apart from the first conveyor where it is rendered nonreusable.

43. A system for rejecting individual containers on a continuously moving high speed bottling line having a detection station and a rejection station, comprising:

a conveyor for conveying a series of containers of substantially uniform diameter in a line unspaced or spaced along a conveyor path at a substantially constant speed;

a detection station located on the conveyor path for identifying a passing object on the conveyor as contaminated;

a rejection station located on the conveyor path at a predetermined spacing downstream from the detection station;

said conveyor continuously conveying the identified container on the conveyor to the rejection station in the same manner and condition as adjacent containers on the conveyor without stopping or forcibly spacing the conveyed containers at any point between the stations; and an optical tracker including a series of light beams arranged along the conveyor between the stations to positively keep track of the identified container from the detection station to the rejection station and for initiating a trigger command;

said rejection station having a ram responsive to said trigger command for selectively ramming an identified container off the conveyor such that adjacent objects are freely conveyed past the rejection station.

44. The system of claim 43, further comprising a reject conveyor for catching the rammed container to transport the rammed container away from the line.

45. The system of claim 44, further comprising means for keeping the rammed container upright while catching the rammed container on the reject conveyor.

46. The system of claim 43, wherein the containers are plastic bottles and said reject conveyor is a neck rail beginning at the rejection station parallel to said ram.

47. The system of claim 43, wherein said rejection station further comprises a gate in the side of the conveyor opposite the ram, and means for opening the gate just before triggering said ram.

48. The system of claim 47, wherein said containers are plastic bottles, and further comprising a neck rail beginning at the rejection station parallel to said ram above said gate to catch bottles rammed off the line.

49. The system of claim 47, further comprising means for issuing said triggering command such that said ram strikes the bottle in a manner which imparts sufficient spin to the bottle as it is rammed off the line to stabilize the bottle and help maintain it upright in flight to the neck rail.

50. The system of claim 43, wherein one of the light beams is associated with the rejection station itself, and said tracker is operable to initiate said trigger command in response to intersection of the beam with a tracked identified container triggering the ramming of the corresponding identified container.

51. The system of claim 43, wherein said containers are bottles, each having a uniform portion of reduced width, and said light beams are aimed across the conveyor to intersect said uniform portion of reduced width on each passing container.

52. The system of claim 43, wherein said light beams are spaced apart by less than the full width of said containers in the direction of the conveyor.

53. The system of claim 51, wherein the beams are spaced apart by about two thirds of the width of the containers.

54. The system of claim 53, wherein the spacing between the stations is at least one and a half container diameters.

55. The system of claim 43, further comprising a side gate on the conveyor at the rejection station, and means for opening the gate just before ramming the identified container so that the identified container is rammed out the side gate, and immediately closing the side gate after the rammed container has cleared the gate, one of the light beams being associated with the rejection station itself, and said tracker initiating a gate command responsive to intersection of the beam with a leading edge of a tracked identified container, said opening means responsive to said gate command for opening said side gate on the conveyor, and said tracker responsive to intersection of the beam with a trailing edge of the tracked identified container issuing said trigger command, triggering the ramming of the corresponding identified container out the open side door.

* * * * *